(12) United States Patent
Lloyd et al.

(10) Patent No.: US 7,660,622 B2
(45) Date of Patent: Feb. 9, 2010

(54) METHOD AND SYSTEM FOR POSITIONING A TRACKING SENSOR FOR OPTIMAL ACCURACY

(75) Inventors: Charles Frederick Lloyd, Reading, MA (US); Yun Wu, Woburn, MA (US); Jon Thomas Lea, Hampstead, NH (US)

(73) Assignee: General Electric Company, Schenectady, NY (US)

( * ) Notice: Subject to any disclaimer, the term of this patent is extended or adjusted under 35 U.S.C. 154(b) by 453 days.

(21) Appl. No.: 10/960,744

(22) Filed: Oct. 7, 2004

(65) Prior Publication Data
US 2006/0079756 A1 Apr. 13, 2006

(51) Int. Cl.
*A61B 5/05* (2006.01)
(52) U.S. Cl. .................. 600/420; 600/415; 600/421; 600/424; 600/426; 600/429; 606/130
(58) Field of Classification Search .............. 600/423, 600/424, 426, 429, 427
See application file for complete search history.

(56) References Cited
U.S. PATENT DOCUMENTS

| 5,592,939 | A | * | 1/1997 | Martinelli | 600/424 |
|---|---|---|---|---|---|
| 6,295,464 | B1 | * | 9/2001 | Metaxas | 600/407 |
| 6,505,065 | B1 | * | 1/2003 | Yanof et al. | 600/427 |
| 6,611,700 | B1 | | 8/2003 | Vilsmeier et al. | |
| 6,731,966 | B1 | * | 5/2004 | Spigelman et al. | 600/407 |
| 2002/0026127 | A1 | * | 2/2002 | Balbierz et al. | 600/567 |
| 2002/0045812 | A1 | * | 4/2002 | Ben-Haim et al. | 600/407 |
| 2005/0054913 | A1 | * | 3/2005 | Duerk et al. | 600/423 |

\* cited by examiner

*Primary Examiner*—Long V Le
*Assistant Examiner*—Ellsworth Weatherby
(74) *Attorney, Agent, or Firm*—McAndrews, Held & Malloy, Ltd.; Peter J. Vogel; Michael A. Dellapenna

(57) ABSTRACT

The present invention provides a method for positioning an electromagnetic tracking sensor. The method includes attaching a sensor to an anatomy, obtaining an image of the anatomy, indicating a size of each of a plurality of volumes on the image, where the volumes include a smaller and larger volume, and making a determination of whether a region of interest is encompassed by one or more of the volumes. The present invention also provides a system for positioning an electromagnetic tracking sensor. The system includes a sensor attached to a patient anatomy, an imaging modality obtaining an image of the anatomy, an image processor indicating a size of each of a plurality of volumes on the image, where the plurality of volumes includes a smaller and larger volume, and an operator making a determination of whether a region of interest is encompassed by one or more of the volumes.

25 Claims, 6 Drawing Sheets

METHOD AND SYSTEM FOR POSITIONING A TRACKING SENSOR FOR OPTIMAL ACCURACY

RELATED APPLICATIONS

Not applicable.

FEDERALLY SPONSORED RESEARCH OR DEVELOPMENT

Not applicable.

BACKGROUND OF THE INVENTION

The present invention generally relates to sensor tracking in a medical procedure. Specifically, the present invention provides a method and system for positioning a tracking sensor for optimal accuracy.

Figure 1:
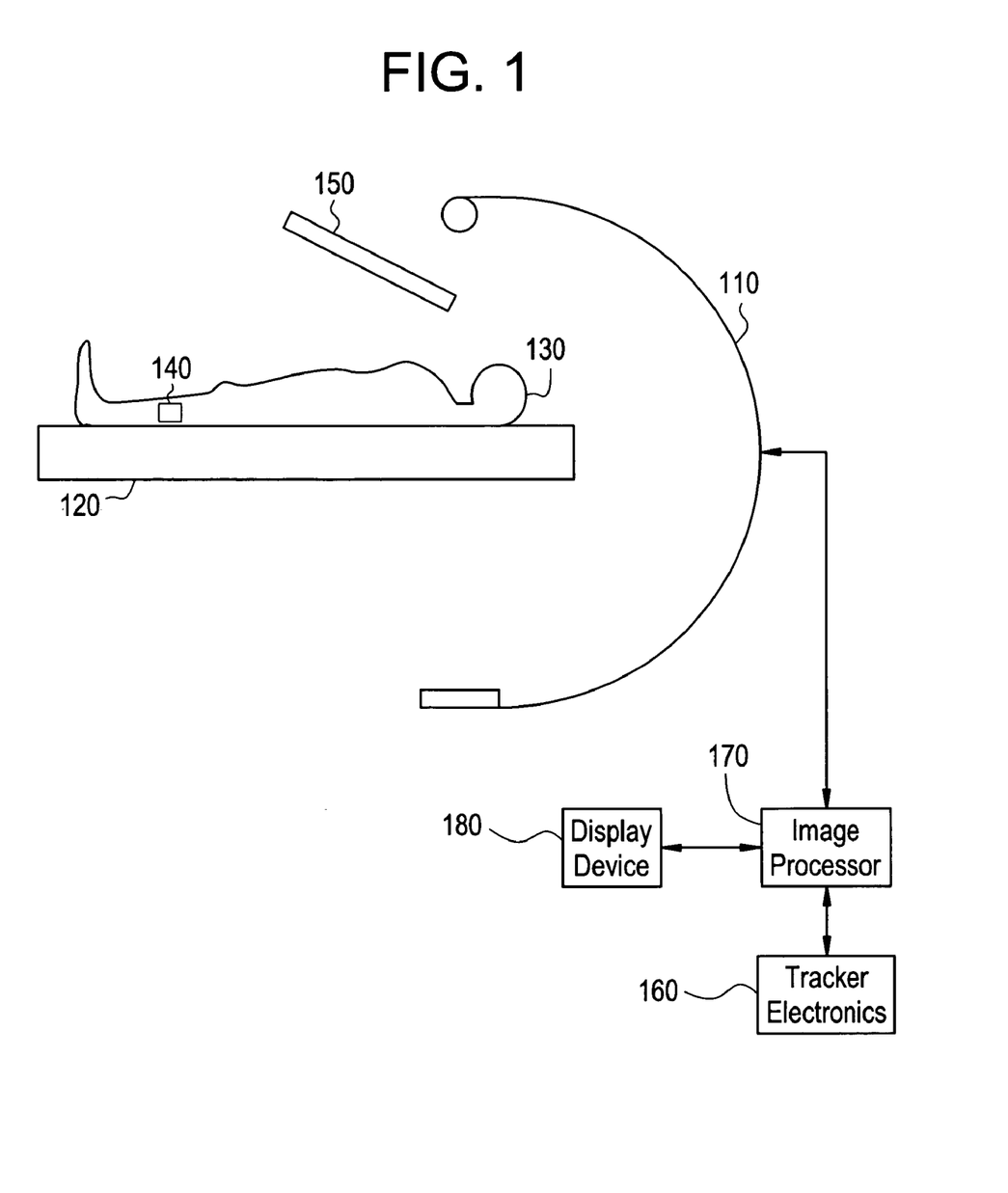
FIG. 1 illustrates an exemplary tracking system.

FIG. 1 illustrates an exemplary tracking system 100. System 100 includes an imaging device 110, a table 120, a patient 130, a tracking sensor 140, a medical device or implant 150, tracker electronics 160, an image processor 170, and a display device 180. Imaging device 110 is depicted as a C-arm useful for obtaining x-ray images of an anatomy of patient 130, but may be any imaging device 110 useful in a tracking system. Imaging device or modality 110 is in communication with image processor 170. Image processor 170 is in communication with tracker electronics 160 and display device 180. Tracker electronics 160 is in communication (not shown) with one or more of a tracking sensor attached to imaging modality 110, a tracking sensor attached to medical instrument 150 and sensor 140.

Sensor 140 is placed on patient to be used as a reference frame in a surgical procedure. For example, sensor 140 may be rigidly fixed to patient 130 in an area near an anatomy where patient 130 is to have an implant 150 inserted or an instrument 150 employed in a medical procedure. The instrument or implant 150 may also include a sensor, thereby allowing for the position and/or orientation of the implant or instrument 150 to be tracked relative to the sensor 140. Sensor 140 may include either a transmitting or receiving sensor, or include a transponder.

Typically, in operation, imaging modality 110 obtains one or more images of a patient anatomy in the vicinity of sensor 140. Tracker electronics 160 may track the position and/or orientation of any one or more of imaging modality 110, sensor 140, and instrument 150 relative to each other and communicate such data to image processor 170.

Imaging modality 110 can communicate image signals of a patient's anatomy to the image processor 170. Image processor 170 may then combine one or more images of an anatomy with tracking data determined by tracker electronics 160 to create an image of the patient anatomy with one or more of sensor 140 and instrument 150 represented in the image. For example, the image may show the location of sensor 140 relative to the anatomy or a region of interest in the anatomy.

Sensor 140 and sensors attached or embedded in an implant or medical instrument may be electromagnetic sensors. However, frequently a surgical environment such as system 100 includes several items that may cause interference in the tracking of a sensor relative to another sensor 140. For example, any metal object in the vicinity of the sensors may result in interference to the accurate measurement of one sensor relative to another. Frequently tables 120, imaging devices 110 and other medical instruments 150 contain metal that interfere with such tracking.

Therefore, in order to obtain increased accuracy of tracking an implant or instrument 150 relative to a sensor 140, sensor 140 should be placed as close as possible to a region of interest in a patient 130. For example, as the accuracy of electromagnetic tracking sensors (such as sensor 140) decreases as the distance between sensor 140 and another sensor increases, it is desirable to locate sensor 140 as close to the region of interest as possible.

Current methods and systems include attaching the transmitting sensor 140 to a rigid point of a patient 130. This typically involves fixing sensor 140 onto a bone of the patient 130. A sensor attached to the instrument or implant 150 is then examined to determine if accurate tracking data is obtained from one or more of sensor 140 and the sensor attached to the instrument/implant 150. If inaccurate measurements are obtained (due to interference or otherwise), then sensor 140 must be detached from patient 130 and re-located. For example, in order to rigidly fix sensor 140 to a patient's bone, a surgeon has to cut into the patient. If the sensor 140 is not properly fixed to the bone, the surgeon must detach the sensor 140 from the patient, make another incision into the patient, and re-fix the sensor 140 to the patient. Such a trial-and-error process can result in unnecessary extended periods of time for surgery and unnecessary incisions into a patient anatomy.

Other methods and systems may measure the anticipated accuracy of a sensor 140 fixed to a patient anatomy. Specifically, current methods and systems fix sensor 140 to an anatomy, take several images of the anatomy (while tracking the position of sensor 140 relative to another point, such as the imaging device or while tracking the position of the imaging device relative to sensor 140), and display an estimation of probable tracking inaccuracies. For example, the display may include an image of the patient anatomy with indicators located on the image at various points. The indicators include an estimation of how inaccurate the tracking of sensor 140 may be at that point. For example, one indicator located near the center of the displayed image may indicate that the tracking of a medical device or implant relative to sensor 140 may be inaccurate by up to 2 mm. Another indicator located near the edge of the displayed image may indicate that the tracking of a medical device or implant relative to sensor 140 at that point may be inaccurate by up to 10 mm. In this way, current method and systems may notify a surgeon of the estimated tracking inaccuracies at various points relative to the patient anatomy.

However, these systems and methods do not provide for the positioning of sensor 140 close to a region of interest to increase the accuracy of the tracking system. As described above, these systems and methods merely indicate how inaccurate the tracking of one point relative to a sensor 140 may be at various points. In this way, current systems and methods estimate tracking inaccuracies instead of increasing the accuracy of the tracking system.

Thus, a need exists for a method and system for positioning an electromagnetic tracking transmitter in order to increase the accuracy of a tracking system. Such a method and system can provide for increased accuracy in tracking measurements during a medical procedure by placing a tracking sensor in a position of increased accuracy for electromagnetic tracking measurements. In addition, such a system and method can decrease the time of surgery and amount of invasive procedures into a patient anatomy while increasing the accuracy of a tracking system.

BRIEF SUMMARY OF THE INVENTION

The present invention provides a method for positioning an electromagnetic tracking sensor. The method includes attaching a sensor to a patient anatomy, obtaining an image of the anatomy, indicating a size of each of a plurality of three-dimensional volumes on the image, where the plurality of volumes include a smaller and larger volume, and making a determination of whether a region of interest is encompassed by one or more of the volumes.

The present invention also provides a system for positioning an electromagnetic tracking sensor. The system includes a sensor attached to a patient anatomy, an imaging modality obtaining an image of the anatomy, an image processor indicating a size of each of a plurality of three-dimensional volumes on the image, where the plurality of volumes includes a smaller and larger volume, and an operator of the system making a determination of whether a region of interest is encompassed by one or more of the volumes.

The present invention also provides a method for optimizing a tracking sensor position. The method includes attaching a tracking sensor to a patient anatomy, imaging the anatomy with a plurality of images, identifying a preferred volume and an outer volume in the plurality of images, and repositioning the sensor based on a comparison of a location of a region of interest in the anatomy and locations of the first and second volumes in the plurality of images.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

As described above, tracking systems typically have several sources of interference with electromagnetic tracking of one sensor relative to another. In addition, electromagnetic tracking sensors tend to be accurate over a small range and lose their accuracy as one sensor moves farther away from another. However, by locating a region of interest in an anatomy of a patient in a close proximity to a sensor, the effects of interference on the tracking system may be greatly reduced.

As described above, sensor 140 can include a transmitting or receiving sensor, or a transponder. Sensor 140 may be used in a tracking system such as illustrated in FIG. 1 and as described above.

A surgeon first attaches sensor 140 to an anatomy of a patient. The patient anatomy may include a region of interest. Sensor 140 may be attached in removable state. For example, sensor 140 may be temporarily affixed to the patient by use of an adhesive, for example. In this way, sensor 140 may be easily removed and repositioned if needed.

Next, an imaging device 110 obtains one or more images of the patient anatomy. As described above, imaging device 110 can be imaging modality useful in a tracking system. For example, imaging device 110 can include a C-arm x-ray imaging modality.

The images can be obtained at various angles with respect to each other. For example, imaging device 110 can obtain two images orthogonal to each other. However, a greater number of images may be obtained. In addition, the angular difference between the images may vary from 90° and may be any angle, such as 45°, for example. A user may therefore obtain multiple views at angles that visualize particular aspects of a patient anatomy.

While imaging device 110 obtains the images, the position of the imaging device 110 relative to sensor 140 is tracked for each image. The imaging device 110 position can be tracked relative to sensor 140 by affixing another sensor to imaging device 110, for example. A device such as tracker electronics 160 known to those of ordinary skill in the art can be used to track the position and/or orientation of imaging device 110 relative to sensor, for example. Tracker electronics 160 can communicate the position and/or orientation data to an image processor 170, such as described in FIG. 1.

Once imaging device 110 has obtained at least one image, the image(s) are communicated to an image processor 170, such as described in FIG. 1. Image processor 170 may then combine the images and the tracking data to create an image to be displayed on a display device 180. The display device 180 can be any device capable of displaying an image to a user. For example, the display device can include a computer monitor. The displayed image can include representations of sensor 140 and/or a medical instrument 150 based on at least the tracking data.

Typically, tracking measurements are more accurate within a given distance of sensor 140. For example, within a given distance of a sensor 140, electromagnetic interference may be minimized or constitute a lesser component of the magnetic field measured by sensor 140 or some other component of the tracking system.

A constant distance from sensor 140 in three dimensions can include a sphere, for example. In an embodiment, the present invention includes two or more spheres that represent two or more constant distances from sensor 140. For example, a smaller sphere may be labeled as an alpha sphere and a larger sphere may be labeled as a beta sphere. In this way, the alpha sphere can include a constant distance from sensor 140 that is smaller than the constant distance from sensor 140 included in the beta sphere.

However, the present invention is not to be limited to spheres. Any useful geometric indicator may be useful in the present invention to represent a distance from sensor. For example, the alpha and beta spheres may be replaced by ellipsoids, cubes, or any other three dimensional geometric shape.

In addition, the present invention is not to be limited to two geometric shapes representing various distances from sensor 140. For example, an embodiment of the present invention may include only a single sphere (for example, the alpha sphere) without any additional spheres or shapes. Further, the present invention may include more than two geometric shapes, for example.

The alpha and beta spheres each or collectively may represent volumes surrounding sensor 140 where electromagnetic tracking of sensor 140 relative to a medical device or implant 150 (or of device/implant 150 relative to sensor 140) is highly accurate. For example, the alpha and/or spheres can include one or more distances from sensor 140 where electromagnetic interference to electromagnetic tracking is reduced or constitutes a lesser component of the measured magnetic field. The alpha and/or beta sphere may therefore be a useful indicator of a "sweet spot" for purposes of increased accuracy in electromagnetic tracking systems.

In general, in order to increase tracking accuracy, an operator of a tracking system may desire that a region of interest of a patient be located within one or more of the alpha and beta spheres. For example, in the insertion of an artificial hip into a patient, sensor 140 may be attached to a patient. Another tracking sensor may be attached or embedded in the hip implant, for example. As the implant is inserted into the patient, the surgeon may employ the tracking system to track the position and/or orientation of the hip implant in order to ensure proper alignment and placement of the hip implant, for example. The surgeon typically desires that the volume of the patient in which the implant sensor is located have little to no electromagnetic interference. Such a volume may be considered a "region of interest". The surgeon may then desire for the region of interest to be as close as possible to sensor 140. In this way, the surgeon may employ the present invention to locate the region of interest within one or more of the alpha and beta spheres.

Figure 2:
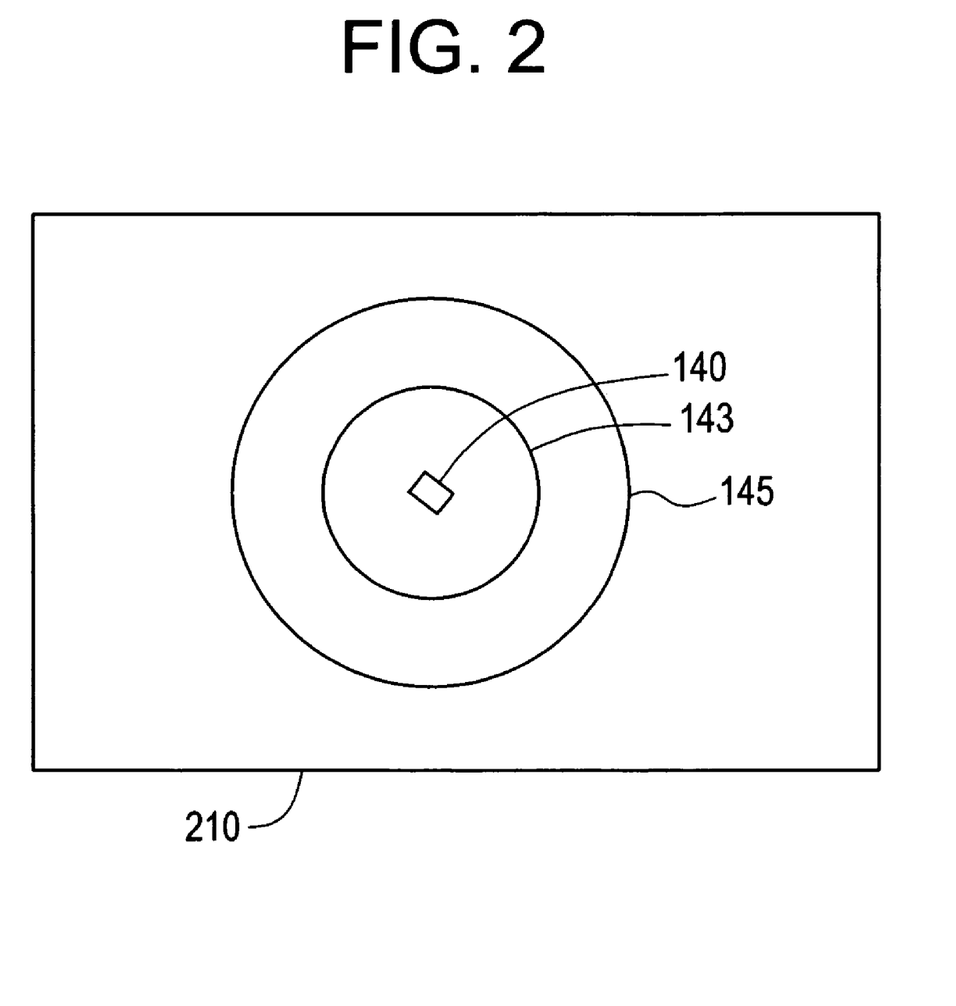
FIG. 2 illustrates a schematic diagram of an exemplary image 210 obtained by the present invention used in accordance with an embodiment of the present invention.

FIG. 2 illustrates a schematic diagram of an exemplary image 210 obtained by the present invention used in accordance with an embodiment of the present invention. Image 210 includes a representation of sensor 140, an alpha circle 143, and a beta circle 145. Alpha and beta circles 143, 145 are two-dimensional representations of the alpha and beta spheres, respectively. The alpha and beta circles 143, 145 may be concentric with sensor 140 acting as a common center point. However, as described above, various geometric shapes may be used in accordance with the present invention. Therefore, while circles 143, 145 in FIG. 2 represent the alpha and beta spheres, other shapes may be used, such as squares representing cubes, for example.

The alpha and beta circles 143, 145 may be marked on an image by an image processor 170. For example, the image processor 170 can draw circles 143, 145 based on two distances (that define the alpha and beta spheres, as described above) stored in a memory and a tracked position and/or orientation of sensor 140 relative to imaging modality 110 (or modality 110 relative to sensor 140).

A surgeon may use image 210 and alpha and beta circles 143, 145 to determine whether one or more of the alpha and beta spheres include a region of interest in a two dimensional plane represented by image 210. For example, if a region of interest is located within one or more of the alpha and beta circles 143, 145 in image 210, a surgeon can therefore know that the region of interest is located within one or more of the spheres 143, 145 in the two dimensional plane represented by image 210.

By obtaining additional images at various angles with respect to each other and indicating the limits of spheres 143, 145 in each two dimensional image, a surgeon can obtain additional details on the proximity of the region of interest to one or more of the alpha and beta spheres in additional two dimensional planes. The surgeon may therefore obtain a better estimation of the proximity of the region of interest to the alpha and beta spheres in three dimensions, for example.

In general, the alpha sphere may be considered to be a "bulls eye" or target sensor 140 volume. For example, the alpha sphere can represent the volume in which a surgeon prefers the region of interest to be located. The beta sphere may be considered a discretionary or "outer limit" sensor 140 volume. For example, the beta sphere can represent the outer edges of a volume in which the surgeon requires the region of interest to be located.

In an embodiment of the present invention, the beta circle 145 may act as a discretionary point at which a surgeon may determine whether sensor 140 needs to be repositioned. For example, a surgeon may obtain a first image where a region of interest is located within the alpha circle 143. However, upon obtaining a second image, the surgeon may discover that the region of interest is located with the beta circle 145, but outside of the alpha circle 143. The surgeon may then employ his or her discretion to determine whether sensor 140 needs to be repositioned. The surgeon may consider the presence of sensor 140 within the beta circle 145 in the second image to be satisfactory as sensor 140 is located within the alpha circle 143 in the first image. However, the surgeon may also consider the presence of sensor 140 within the beta circle 145 in any image to be unsatisfactory, and may reposition sensor 140 accordingly.

A surgeon may employ the present invention to improve the accuracy of a tracking system by obtaining a plurality of images detailing the relative proximity of a region of interest to the alpha and beta spheres as follows. For example, a surgeon may obtain a first image and determine that a region of interest is not located within either the alpha or beta spheres. As sensor 140 is easily detached and re-attached to the patient, the surgeon may then move sensor 140 to another position on the patient anatomy.

A display device displaying the first image may then represent the movement of sensor 140 relative to the patient or some other fixed point (such as, for example, the imaging device 110) by moving the alpha and beta circles 143, 145 according to the movement of sensor 140. For example, if a surgeon moves sensor 140 20 mm along a limb of a patient, the display device may move the alpha and beta circles 143, 145 a corresponding distance in first image. In this way, a surgeon may quickly place sensor 140 in a more accurate tracking position in at least one two dimensional plane (represented by the active image).

The present invention thus provides for the ability for a surgeon to obtain an image of an initial placement of a sensor 140, the determination of whether sensor 140 needs to be moved, and, if so, the resulting movement of sensor 140. The surgeon is therefore able to move the tracking frame of reference (represented by sensor 140) based on at least one or more images of a patient anatomy.

Figure 3:
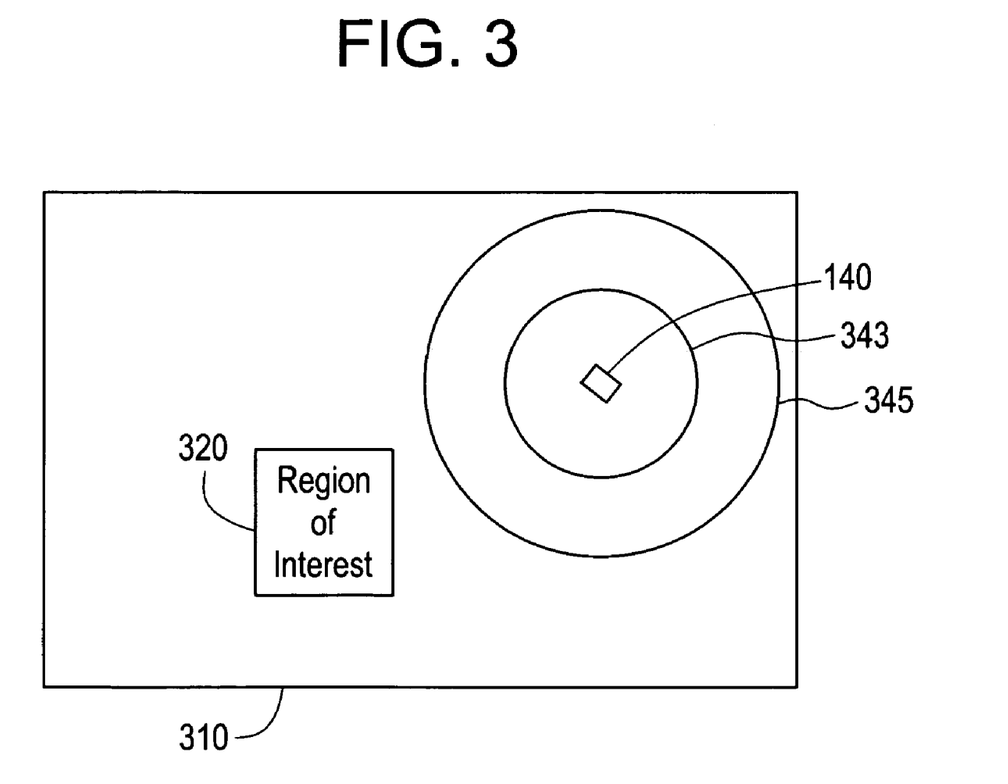
FIG. 3 illustrates a schematic diagram of a first image of a patient's anatomy in a first two-dimensional plane according to an embodiment of the present invention.

The present invention may be illustrates by the following example. A surgeon temporarily attaches sensor 140 to a patient anatomy and obtains at least one image, for example a first image 310. FIG. 3 illustrates a schematic diagram of first image 310 of a patient's anatomy in a first two-dimensional plane according to an embodiment of the present invention. First image 310 includes sensor 140, a first alpha circle 343, a first beta circle 345, and a region of interest 320. The label "first" for alpha and beta circles 343, 34.5 is used to indicate which image and which two dimensional plane the circles 343, 345 are associated with.

The surgeon examines image 310 to determine whether region 320 is located within one or more of the alpha and beta circles 343, 345. For example, in FIG. 3 region 320 is located outside both circles 343, 345. The sensor 140 therefore needs to be re-positioned. The surgeon may then detach or remove sensor 140 from the patient. The sensor 140 may then be re-attached to the patient in an attempt to locate region 320 within one or more of circles 343, 345. For example, the surgeon may move sensor 140 while looking at image 310 displayed on a display device. As sensor 140 is moved, the alpha and beta circles 343, 345 correspondingly move in image 310. The surgeon may therefore move sensor 140 so that one or more of the alpha and beta circles 343, 345 encompass region 320, for example.

Figure 4:
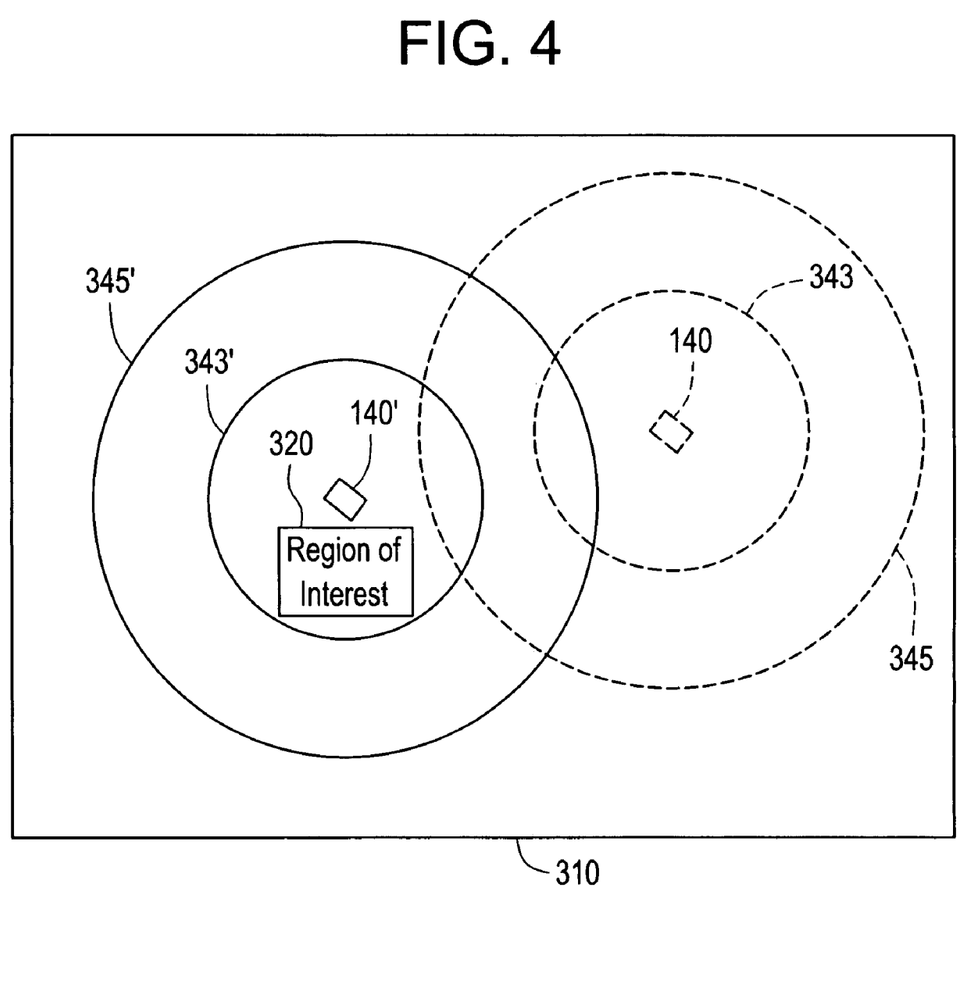
FIG. 4 illustrates an image after a reference frame represented by a sensor has been moved to encompass a region of interest in accordance with an embodiment of the present invention.

For example, FIG. 4 illustrates image 310' after a reference frame represented by sensor 140 has been moved to encompass region of interest 320 in accordance with an embodiment of the present invention. Image 310' of FIG. 4 includes first alpha and beta circles 343, 345, sensor 140, and region 320. Image 310' also includes alpha and beta circles 343', 345' and sensor 140'. Circles 343' and 345' and sensor 140' represent the displayed location of alpha and beta circles 343, 345 and sensor 140 after sensor 140 has been moved. Therefore, a surgeon can witness the movement of alpha and beta circles 343, 345 and sensor 140 from their initial positions (for example, circles 343, 345 and sensor 140) to the new positions (for example, circles 343', 345' and sensor 140') on a display device while sensor 140 is moved.

Figure 5:
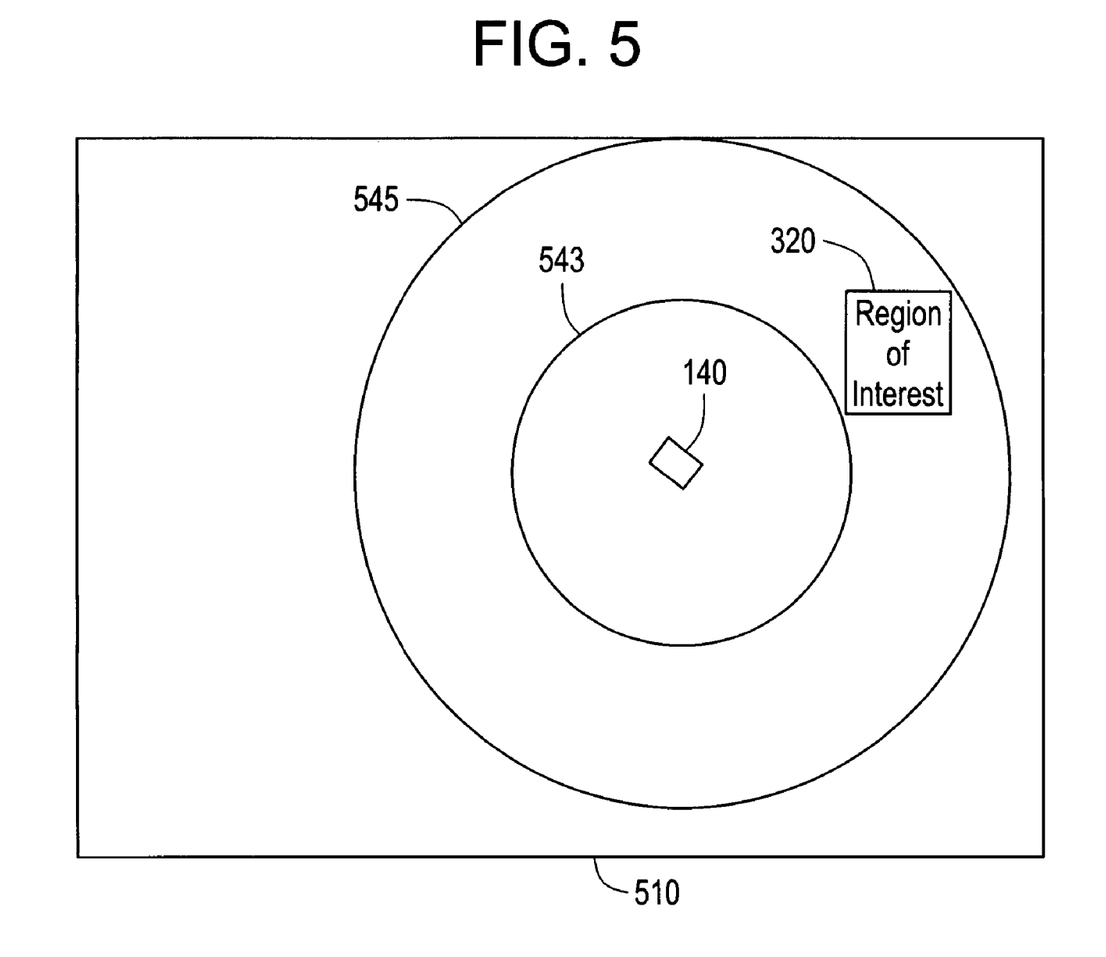
FIG. 5 illustrates a schematic diagram of a second image according to an embodiment of the present invention.

The surgeon may then wish to obtain a second image 510 a given angular distance from first image 310. FIG. 5 illustrates a schematic diagram of a second image 510 according to an embodiment of the present invention. Second image 510 includes sensor 140, a second alpha circle 543, a second beta circle 545, and region of interest 320.

The label "second" for alpha and beta circles 543, 545 is used to indicate which image and which two dimensional plane the circles 543, 545 are associated with. For example, as image 310 may be associated with a first two-dimensional plane, second image 510 may similarly be associated with a second, different two-dimensional plane orthogonal to that of first image 310. In such an example, first image 310 may be an AP x-ray image obtained by a C-arm device while second image 510 may be a lateral x-ray image obtained by the C-arm device.

Similar to as described above, a surgeon may examine second image 510 in order to determine the proximity of region 320 to sensor 140. In second image 510, for example, region 320 is located within beta circle 545, but not within alpha circle 543. As described above, the surgeon may then, in his or her discretion, decide whether to reposition sensor 140 or whether to rigidly fix sensor 140 to the patient. For example, as region 320 is located within alpha circle 343' in FIG. 4, sensor 140 is optimally located in the two-dimensional plane of image 310. However, region 320 is located within beta circle 545, but not alpha circle 543, of image 510. Therefore, sensor is not optimally located in the two-dimensional plane of image 510. The surgeon may therefore decide whether to reposition sensor 140 so as to more optimally locate region 320 (for example, by placing sensor 140 so that region 320 is in alpha circle 343 of image 310 and alpha circle 543 of image 510) or to rigidly fix sensor 140 in its current position.

Depending upon an operator's requirements of the proximity of region 320 to sensor 140, as few as two images may be required. For example, a surgeon may only examine two images (such as images 310 and 510, for example) to determine the proximity between region 320 and sensor 140. However, a surgeon may require more images at varying angles to obtain more information concerning the proximity of sensor 140 to region 320 in various planes.

In addition, the surgeon may use different sized-spheres (or other geometric shapes) for different two-dimensional planes. For example, a surgeon may use a smaller-sized alpha sphere (and/or beta sphere) in one image while using a larger alpha sphere (and/or beta sphere) in another image.

Figure 6:
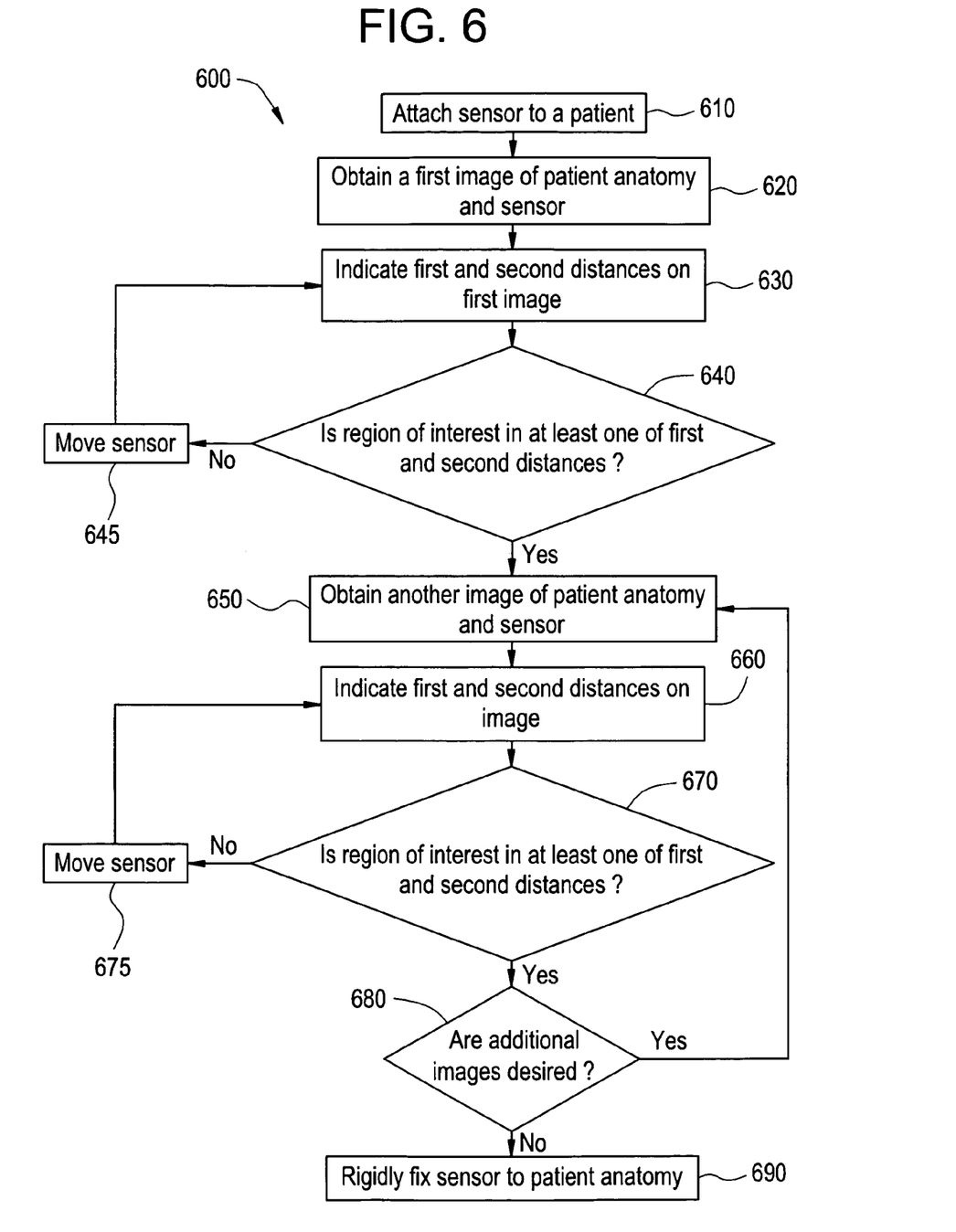
FIG. 6 illustrates a flowchart for a method for positioning a tracking sensor according to an embodiment of the present invention.

FIG. 6 illustrates a flowchart for a method 600 for positioning a tracking sensor according to an embodiment of the present invention. First, at step 610, a sensor 140 is attached to a patient. As described above, sensor 140 is removably attached to the patient.

Next, at step 620, a first image 310 of a patient's anatomy and sensor 140 is obtained, as described above. The position of the imaging device 110 may be tracked relative to sensor 140, for example. If one or more of a region of interest 320 and sensor 140 are not visible in first image 310, then sensor 140 may be moved or the imaged area of patient may be changed before re-obtaining first image 310. In this way, step 620 may repeat until at least one of region 320 and sensor 140 are visible in first image 310.

At step 630, an alpha circle 343 and a beta circle 345 are drawn onto first image 310, as described above. Circles 343, 345 may represent alpha and beta spheres, respectively, for example.

Next, at step 640, an operator of the tracking system examines first image 310 to determine whether region 320 in a patient anatomy is located within one or more of the alpha and beta spheres in the two-dimensional plane represented by image 310. The surgeon or operator may perform this step by determining whether region 320 is located within one or more of alpha and beta circles 343 and 345, for example, as described above. Based on at least this determination, method 600 may proceed to either step 650 (if region 320 is located within one or more of alpha and beta spheres) or to step 645 (if region 320 is not located within either of the alpha and beta spheres).

If method 600 proceeds to step 645, a surgeon or operator of the system moves sensor 140 so that sensor 140 is closer in proximity to region 320 in the two-dimensional plane represented by the image. Method 600 then proceeds to step 630, where the alpha and beta circles 343, 345 (representing the alpha and beta spheres, respectively) are drawn onto image 310 in their new position relative to region 320. Method 600 then again proceeds to step 640, where an operator or surgeon again determines whether either alpha or beta circles 343, 345 include region 320. In this way, method 600 may include a loop from step 640 to step 645 to step 630 when region 320 is not within one or more of the alpha and beta spheres within the two-dimensional plane represented by image 310.

Next, at step 650, another image 510 of the patient anatomy and sensor 140 is obtained. As described above, image 510 may be obtained at a different angle than image 310. For example, images 310 and 510 may be mutually orthogonal.

Next, at step 660, alpha and beta circles 543, 545 (representing the alpha and beta spheres in the two-dimensional plane of image 510) are drawn on image 510, similar to step 630 and as described above.

In another embodiment of the present invention, an alpha and/or beta circle of one image may be of a different size than an alpha and/or beta circle of another image, as described above.

Next, at step 670, a surgeon or an operator of the tracking system examines image 510 to determine whether region 320 is located within one or more of the alpha and beta spheres. Based on at least this determination, method 600 may proceed to either step 680 (if region 320 is located within one or more of alpha and beta circles 543, 545 representative of the alpha and beta spheres, respectively, in the two-dimensional plane of image 510) or to step 675 (if region 320 is not located within either alpha or beta circle 543 or 545).

In another embodiment of the present invention, a surgeon or operator may proceed to step 680 from step 670 if region 320 is within the alpha circle 343 of the first image 310, but is outside the alpha circle 543 of the second image 510, as long as region 320 is within the beta circle 545 of the second image 510. As described above, the beta circle 345, 545 may therefore be referred to as a discretionary circle.

If region 320 is not located within either circle 543 or 545, or the surgeon or operator determines that sensor 140 is not otherwise close enough to region 320, method 600 proceeds to step 675 where the surgeon or operator may move sensor 140. After sensor 140 is moved, method 600 proceeds to step 660, where alpha and beta circles 543, 545 are again drawn on second image 510 in their new positions. Method 600 may then again proceed to step 670, where the surgeon or operator determines whether region 320 is within close enough proximity to one or more of alpha and beta circles 543, 545, as described above. In this way, method 600 may include a loop from step 670 to step 675 to step 650 when an operator or surgeon determines that region 320 is not within a close enough proximity to sensor 140.

Next, at step 680, the surgeon or operator determines whether to obtain additional images. As described above, additional images at varying angles with respect to each other may be obtained in order to optimally locate sensor 140 relative to region 320. If it is determined that additional images are desired, method 600 may proceed to step 650. If no additional images are desired, method 600 may proceed to step 690.

Next, at step 690, sensor 140 may be rigidly fixed to the patient anatomy and the medical procedure may proceed.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features that come within the spirit and scope of the invention.

What is claimed is:

1. A method for positioning an electromagnetic tracking sensor, said method including:
   determining a region of interest in a patient anatomy, wherein said region of interest represents an area of reduced electromagnetic interference;
   attaching said sensor to said patient anatomy;
   obtaining an image of said anatomy;
   indicating a size of each of a plurality of volumes on said image, said plurality of volumes including a predetermined smaller and larger volume, wherein each volume in said plurality of volumes represents at least one distance from said sensor, wherein said larger volume contains said smaller volume;
   making a determination of whether said region of interest is encompassed by one or more of said volumes; and
   moving said sensor based on at least said making a determination step such that the region of interest is encompassed by at least one of said volumes.

2. The method of claim 1, wherein said volumes are concentric with said sensor located at a center of said volumes.

3. The method of claim 1, wherein said smaller volume represents a distance from said sensor in which said region is preferred to be located.

4. The method of claim 1, wherein said moving step includes moving said sensor if said region is not located within said smaller volume.

5. The method of claim 1, wherein said moving step includes moving said sensor if said region is not located within said larger volume.

6. The method of claim 1, wherein said volumes include at least one sphere.

7. The method of claim 1, wherein said indicating step includes drawing a two-dimensional representation of at least one of said volumes in said image.

8. The method of claim 1, further including:
   obtaining a second image of said anatomy;
   indicating a size of each of a second plurality of volumes on said second image, said second plurality of volumes including a second smaller volume and second larger volume; and
   making a second determination of whether said region is encompassed by one or more of said second volumes.

9. The method of claim 8, further including:
   moving said sensor based on at least one or more of said making a determination step and said making a second determination step.

10. The method of claim 8, wherein said image and said second image are mutually orthogonal.

11. A system for positioning an electromagnetic tracking sensor, said system including:
    a sensor adapted to attach to a patient anatomy;
    an imaging modality adapted to obtain an image of said anatomy;
    an image processor adapted to indicate a size of each of a plurality of volumes on said image, said plurality of volumes including a predetermined smaller and larger volume, wherein each volume in said plurality of volumes represents at least one distance from said sensor, wherein said larger volume contains said smaller volume, wherein said image processor is further adapted to indicate a region of interest in said patient anatomy to aid in making a determination of whether said region of interest is encompassed by one or more of said volumes, wherein said region of interest represents an area of reduced electromagnetic interference, wherein said image processor is further adapted to aid in making a decision of whether to move said sensor based on at least said determination of whether said region of interest is encompassed by one or more of said volumes, and wherein said sensor is further adapted to be moved based on at least said decision such that the region of interest is encompassed by at least one of said volumes.

12. The system of claim 11, wherein said volumes are concentric with said sensor located at a center of said volumes.

13. The system of claim 11, wherein said smaller volume represents a distance from said sensor in which said region is preferred to be located.

14. The system of claim 11, wherein said image processor is further adapted to aid in making a decision of whether to move said sensor based on whether said region is located within said smaller volume.

15. The system of claim 11, wherein said image processor is further adapted to aid in making a decision of whether to move said sensor based on whether said region is located within said larger volume.

16. The system of claim 11, wherein said volumes include at least one sphere.

17. The system of claim 11, wherein said image processor draws a two-dimensional representation of at least one of said volumes in said image.

18. The system of claim 11, wherein said imaging modality is further adapted to obtain a second image of said anatomy and said image processor is further adapted to indicate a size of each of a second plurality of volumes on said second image to aid in making a second determination of whether said region is encompassed by one or more of said second volumes, wherein said second plurality of volumes include a second smaller volume and second larger volume.

19. The system of claim 18, wherein said image processor is further adapted to aid in making a decision of whether to move said sensor based on at least one or more of said determination and said second determination.

20. The system of claim 18, wherein said image and said second image are mutually orthogonal.

21. A method for optimizing a tracking sensor position, said method including:
  determining a region of interest in a patient anatomy, wherein said region of interest represents an area of reduced electromagnetic interference;
  attaching said sensor to said patient anatomy;
  imaging said anatomy with a plurality of images;
  identifying a predetermined preferred volume and a predetermined outer volume in said plurality of images, wherein said preferred and outer volumes each represents at least one distance from said sensor, wherein the outer volume contains the preferred volume;
  making a determination of whether said region of interest is encompassed by one or more of said volumes; and
  moving said sensor based on at least said making a determination step such that the region of interest is encompassed by said preferred volume.

22. The method of claim 21, wherein said imaging step includes imaging said anatomy with at least two mutually orthogonal images.

23. The method of claim 21, wherein said attaching step includes temporarily attaching said sensor.

24. The method of claim 21, wherein said preferred and outer volumes are spheres with said sensor located at a center of said spheres.

25. The method of claim 21, wherein said moving step includes moving said sensor when said region of interest is located outside said outer volume in at least one of said images.

\* \* \* \* \*